US010660927B2

(12) United States Patent
Kang

(10) Patent No.: US 10,660,927 B2
(45) Date of Patent: May 26, 2020

(54) **COMPOSITION, CONTAINING EXTRACTS OF *DIPSACUS ASPEROIDES* AND *CYNANCHUM WILFORDII* AS ACTIVE INGREDIENTS, FOR PROMOTING MOTOR ABILITY AND MUSCLES**

(71) Applicant: BRAINON INC

(72) Inventor: Yongkoo Kang, Seoul (KR)

(73) Assignee: BRAINON INC., Cheongji-si, Chungcheongbuk-Do (KR)

( * ) Notice: Subject to any disclaimer, the term of this patent is extended or adjusted under 35 U.S.C. 154(b) by 136 days.

(21) Appl. No.: 15/742,827

(22) PCT Filed: Jul. 7, 2016

(86) PCT No.: PCT/KR2016/007344
§ 371 (c)(1),
(2) Date: Jan. 8, 2018

(87) PCT Pub. No.: WO2017/010735
PCT Pub. Date: Jan. 19, 2017

(65) Prior Publication Data
US 2019/0000906 A1 Jan. 3, 2019

(30) Foreign Application Priority Data

Jul. 10, 2015 (KR) .................. 10-2015-0098183

(51) Int. Cl.
| | | |
|---|---|---|
| *A61K 36/00* | (2006.01) | |
| *A61K 36/27* | (2006.01) | |
| *A61K 36/53* | (2006.01) | |
| *A23L 33/105* | (2016.01) | |
| *A61P 21/00* | (2006.01) | |

(52) U.S. Cl.
CPC ............ *A61K 36/53* (2013.01); *A23L 33/105* (2016.08); *A61K 36/27* (2013.01); *A61P 21/00* (2018.01); *A23V 2002/00* (2013.01); *A23V 2200/316* (2013.01); *A23V 2250/21* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,984,405 B1 | 1/2006 | Kim | |
| 7,763,284 B2 * | 7/2010 | Kim ..................... | A23L 33/16 424/725 |
| 7,854,948 B2 | 12/2010 | Slimak | |
| 2012/0015059 A1 | 1/2012 | Kim et al. | |
| 2015/0125558 A1 | 5/2015 | Hong | |

FOREIGN PATENT DOCUMENTS

| | | |
|---|---|---|
| CN | 103877235 A | 6/2014 |
| CN | 104116923 A | 10/2014 |
| JP | 2004-518647 A | 6/2004 |
| JP | 2005-539007 A | 12/2005 |
| JP | 2006-335721 A | 12/2006 |
| JP | 2008-007473 A | 1/2008 |
| JP | 2008-019170 A | 1/2008 |
| JP | 2008-255078 A | 10/2008 |
| JP | 2012-521413 A | 9/2012 |
| KR | 1020020090077 A | 11/2002 |
| KR | 100406837 B1 | 11/2003 |
| KR | WO2004/035074 A1 | 4/2004 |
| KR | 10-0696830 | 3/2007 |
| KR | 100696830 B1 | 3/2007 |
| KR | 10-0714414 | 5/2007 |
| KR | 100714464 B1 | 5/2007 |
| KR | 10-2009-0086671 A | 8/2009 |
| WO | 02/47702 A1 | 6/2002 |
| WO | 2004/012754 A1 | 2/2004 |
| WO | 2004/035074 A1 | 4/2004 |
| WO | 2008069636 A1 | 6/2008 |

OTHER PUBLICATIONS

Natural Endotech Co. Ltd (Development of functional feed additive for he improvement of fattening and beef quality of castrated beef by the natural extract having estrogen-like action phytoestrogen, Apr. 24, 2009,Research Project Report (Ministry for Food, Agriculture, Forestry and Fisheries)p. 1-85 (Year: 2009).*
Naturalendotech, "Development of Functional Feed Additive for the improvement of fattening and beef quality of castrated beef cattle by the natural extracts having estrogen-like action of phytoestrogen",Apr. 24, 2009, Research Project Report, See pp. 1-85.
Office Action issued for Russian Patent Application No. 2018104977(007512) dated Feb. 7, 2019.
Office Action issued for Australian Patent Application No. 2016293900 dated Mar. 6, 2019.
Office Action issued for Japanese Patent Application No. 2018-521165 dated Dec. 4, 2018.
Search Report issued for European Patent Application No. 16 824 652.8 dated Mar. 7, 2019.
Kim, Joo Min; "Effects of Feed Additive from Phlomis Umbrosa Turcz. and Cynanchum Wilfordii (Gromax®) on Growth Performance, Meat Production and Biochemical Parameters in Broiler"; Aug. 1, 2013, pp. 1-79, Korea.
Chang, A et al. "The Effect of Herbal Extract (EstroG-100) on Pre-, Peri- and Post-Menopausal Women: A Randomized Double-blind, Placebo-controlled Study". Phytotherapy Research, 2012. vol. 26, pp. 510-516; South Korea.
Ki Ho Lee et al; "Evaluation of Effectiveness and Safety of Natural Plants Extract(Estromon) on Perimenopausal Women for 1 Year";Korean Society of Menopause, 2005. vol. 11, pp. 16-26; South Korea.

(Continued)

*Primary Examiner* — Michael Barker
*Assistant Examiner* — Randall Winston
(74) *Attorney, Agent, or Firm* — Rothwell, Figg, Ernst & Manbeck, P.C.

(57) ABSTRACT

The present invention relates to a composition, containing extracts of *Dipsacus asperoides*(*Phlomis umbrosa Turcz*) and *Cynanchum wilfordii* as active ingredients, for promoting exercise ability and/or muscle formation. The intake of the composition according to the present invention promotes motor performance ability, and is useful in the promotion of muscle development.

6 Claims, 2 Drawing Sheets

(56) References Cited

OTHER PUBLICATIONS

"Development of functional feed additive for the improvement of fattening and beef quality of castrated beef cattle by the natural extracts having estrogen-like action of phytoestrogen"; Research Project Report (Ministry for Food, Agriculture, Forestry and Fisheries, (Apr. 24, 2009), pp. 1-85; South Korea.
Kim, M.Y et al; "Skeletal growth and IGF levels in rats after HT042 treatment." Phytotherapy research, 2012. vol. 26 (12): pp. 1771-1778 (Abstract only); South Korea.
Japanese Office Action issued for Japanese Patent Application No. 2018-521165 dated May 28, 2019, 8 pages.

* cited by examiner

[Fig. 1]
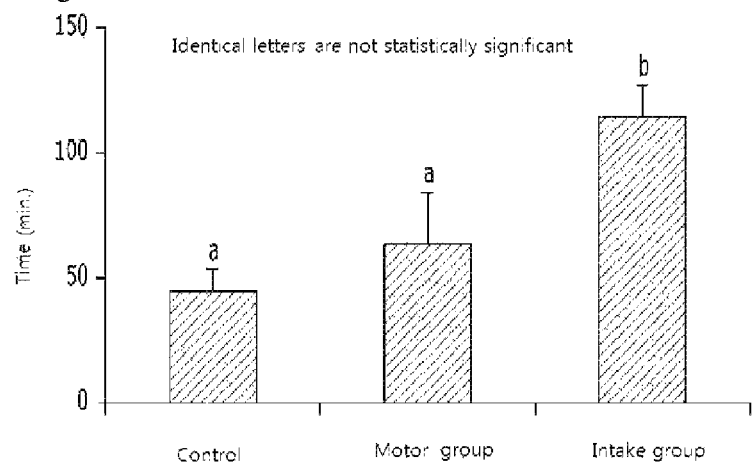
[Fig. 2]
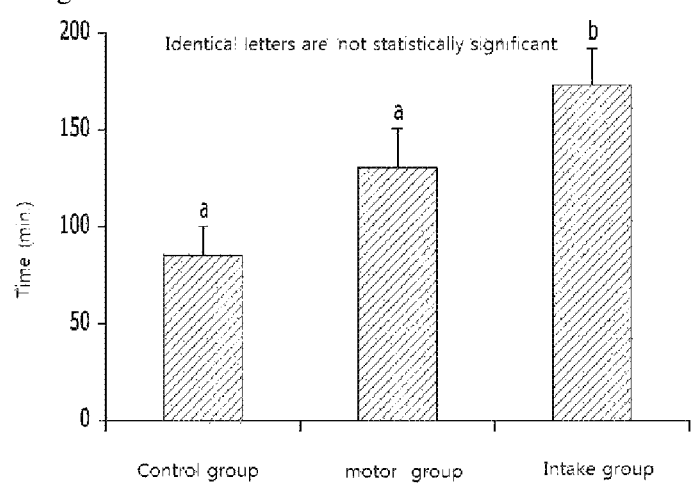

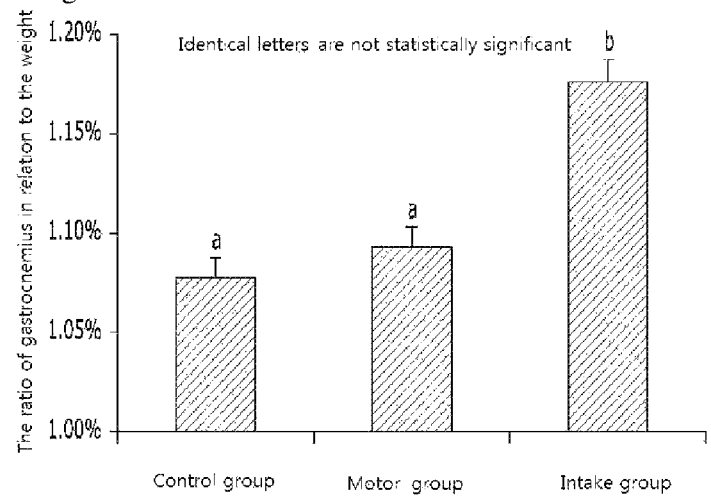
[Fig. 3]

COMPOSITION, CONTAINING EXTRACTS OF *DIPSACUS ASPEROIDES* AND *CYNANCHUM WILFORDII* AS ACTIVE INGREDIENTS, FOR PROMOTING MOTOR ABILITY AND MUSCLES

TECHNICAL FIELD

The present invention relates to a composition for promoting exercise ability and/or muscle development, which contains extracts of *Phlomis umbrosa Turcz* and *Cynanchum wilfordii* as active ingredients.

BACKGROUND ART

In general, if the muscles do not exercise continuously, the function of the muscle is degraded by aging and the muscle mass and neuromuscular junction (motor unit) are decreased, and thus, the vitality of life is reduced and the quality of life drops sharply because the fatigue is easily felt and the body becomes helpless (J. Appl. Physiol. 2003, 95, p 1717-1727). In order to prevent this, it is recommended that the motor (muscle exercise) such as resistance training is to be continuously carried out (Korean Laid-open Patent Publication No. 10-2009-0089815), and the proper dietary treatment is performed together with this. Thus, a regular motor (muscle training) is needed to improve the quality of life of, not only athletes but also the ordinary people that need more energy and endurance in daily life. However, the most modern people being chased by busy life tend to depend on dietary supplements rather than the motor (muscle exercise). Therefore, studies on adjuvant, functional foods, and food composition, etc. for improving the ability for performing the physical motor (muscles) have been continued for a long time, and actually it is known that taking a compound such as steroids, caffeine, etc. increases the motor ability. However, these drugs may be accompanied by fatal side effects and thus their use is extremely limited.

PRIOR PATENT PUBLICATION

Korean Laid-Open Patent Publication No. 1020110079564.

DISCLOSURE

Technical Problem

The present invention is to solve problems mentioned above and is made by the above-mentioned needs, and thus, the object of the invention is to provide a novel composition for promoting the motor ability.

Another object of the present invention is to provide a composition for promoting the muscle development.

Technical Solution

In order to achieve the above objects, the present invention provides the food compositions for promoting the exercise ability, containing the extracts of *Phlomis umbrosa Turcz* and *Cynanchum wilfordii* as the active ingredients.

In one embodiment of the present invention, the extracts of *Phlomis umbrosa Turcz* and *Cynanchum wilfordii* may preferably be extracted with any one of the solvents selected from the group consisting of water or alcohol having 1 to 6 carbon atoms and the mixed solvents thereof, but are not limited thereto.

In the preferable embodiment of the present invention, the mixing ratio of *Phlomis umbrosa Turcz* extract and *Cynanchum wilfordii* extract is preferably 1:0.1 to 1:10 weight ratio (ratio by weight) and more preferably 1:1 weight ratio, but is not limited thereto.

Further, the present invention provides a food composition for promoting muscle development, containing extracts of *Phlomis umbrosa Turcz* and *Cynanchum wilfordii* as active ingredients.

Further, the present invention provides a pharmaceutical composition for promoting exercise ability, containing extracts of *Phlomis umbrosa Turcz* and *Cynanchum wilfordii* as active ingredients.

Further, the present invention provides a pharmaceutical composition for promoting muscle development, containing extracts of *Phlomis umbrosa Turcz* and *Cynanchum wilfordii* as active ingredients.

Hereinafter, the present invention will be described.

The present inventors have conducted a research to search for a natural substance that promotes exercise ability and enhances muscle development and as a result, have identified that the exercise ability is greatly improved and the excellent effect for promoting muscle development is exhibited when taking a mixture of *Phlomis umbrosa Turcz* extract and *Cynanchum wilfordii* extract and completed the present invention.

The compositions according to the present invention for promoting exercise ability or muscle development are not particularly limited in its formulation, but may be, for example, a pharmaceutical composition or a health food composition.

When the composition of the present invention is a pharmaceutical composition, it may be used after formulating it into an oral formulation, external preparation, suppository formulation, sterile injection solution, and the like, according to a conventional method.

In addition, if necessary, one or two more kinds of the following additives may be added and combined to the above composition. As the additives, for example, various kinds of fruit juices such as grapefruit, apple, orange, lemon, pineapple, banana, pea, and the like (a concentrated fruit juice, powdered fruit juice and the like may also be preferred); vitamins (water-soluble and fat-soluble vitamins such as retinol palmitate, riboflavin, pyridoxine, cyanocobalamine, sodium ascorbate, amide nicotinate, calcium pantothenate, folic acid, biotin, cholecalciferol, choline bitartrate, tocopherol, β-carotine and the like); flavors (lemon flavor, orange flavor, strawberry flavor, grapefruit flavor, vanilla essence, and the like); amino acids, nucleic acid and their salts (glutamic acid, sodium glutamate, glycine, alanine, asparginic acid, sodium asparginate, inosinic acid, and the like); plant fiber (polydextrose, pectin, xanthan rubber, glucomannan, alginic acid, and the like); or minerals (sodium chloride, sodium acetate, magnesium sulfate, potassium chloride, magnesium chloride, magnesium carbonate, calcium chloride, dipotassium phosphate, monosodium phosphate, calcium glycerophosphate, sodium ferrous citrate, ferric ammonium citrate, ferric citrate, manganese sulfate, copper sulfate, sodium iodide, potassium sorbate, zinc, manganese, copper, iodine or cobalt, and the like) may be included.

The composition may further include a pharmaceutical adjuvant such as a preservative, a stabilizing agent, a hydrating agent or an emulsifying accelerator, a salt and/or buffer for controlling osmotic pressure, etc. and other therapeutically effective materials, and can be formulated into various administration modes for oral or parental uses according to the conventional methods.

The oral formulation includes for example, a tablet, a pill, a hard and soft capsules, a liquid, a suspension, an emulsion, a syrup, a granule, and the like, and such formulations contain diluents (e.g., lactose, dextrose, sucrose, mannitol, sorbitol, cellulose and glycine), lubricants (e.g., silica, talc, stearic acid and a magnesium or calcium salt thereof and polyethylene glycol), in addition to the effective ingredients. The tablet may further contain a binder such as magnesium aluminum silicate, starch paste, gelatin, tragacanth, methylcellulose, sodium carboxymethylcellulose and polyvinylpyrrolidine, and if necessary, may further contain a pharmaceutical additive, for example, a disintegrating agent such as starch, agar, alginic acid or its sodium salt, absorbents, coloring agent, flavoring agent, sweetener, and the like. The tablet may be prepared by conventional mixing, granulating or coating methods. Also, the representative formulation for parental administration is preferably an aqueous isotonic solution or suspension as a formulation for injection.

In addition, when the composition according to the present invention is a health food composition, it may be formulated into various foods, beverages, chewing gums, teas, a vitamin complex or health functional food, and the like. Since *Cynanchum wilfordii* and *Phlomis umbrosa Turcz* used in the present invention almost free from toxicity and side effect, they can be safely used even for prolonged dosing for preventive purposes.

The health food composition of the present invention does not specifically limit other ingredients except that it contains the extracts of the present invention in the indicated ratio, as the necessary ingredients, and may further contain various flavoring agents or natural carbohydrates, etc. such as a conventional beverage as the additional ingredients. Examples of the natural carbohydrates mentioned above include the conventional sugar such as monosaccharide, for example, glucose, fructose, etc.; disaccharides, for example, maltose, sucrose, etc.; and polysaccharides, for example, dextrin, cyclodextrin, etc., and sugar alcohol such as xylitol, sorbitol, erythritol, etc. In addition to the above-mentioned ingredients, the natural flavoring agent such as taumatin, stevia extract (e.g., rebaudioside A, glycyrrhizin, etc.) and synthetic flavoring agent (saccharin, aspartame, etc.) may be advantageously used as the flavoring agent. The ratio of the above natural carbohydrates is generally about 1~20 g, preferably about 5~12 g per 100 ml of the composition of the present invention.

In addition to the above ingredients, the composition of the present invention may contain various kinds of nutrients, vitamins, minerals (electrolyte), flavoring agent such as a synthetic and natural flavoring agent, coloring agent, flavor enhancer, pectinic acid and its salts, alginic acid and its salts, organic acid, protective colloid thickener, pH adjusting agent, stabilizer, preservative, glycerine, alcohol or carbonation agent used in carbonated drinks, etc. Further, the compositions of the present invention may contain fruit fleshes for preparing the natural fruit juices and fruit juice beverages and vegetable beverages. Such ingredients may be used independently or in combination. Although the ratio of such an additive is not so important, the additive is generally selected from the range of 0~20% by weight based on the total weight of the composition of the present invention.

A dose of said extracts of the present invention may be limited within the range of the level of the skilled person in the relevant art. Although the dose of the composition according to the present invention per a day can be varied according to various factors such as a progression degree of obesity, period of onset, age, health condition, complication, etc. of the subject to be administrated, a total of 1 to 5000 mg/kg, preferably 30 to 1000 mg/kg of the composition combined in the weight ratio mentioned above may be administered, in a divided amount of 1 or 2 times a day, and the said dose is not intended to limit the scope of the present invention in any way.

The contents of the extracts of the present invention are not particularly limited, but are preferable to be contained in the range of 10~90% by weight based on the total weight of the composition. It can provide the health food composition or pharmaceutical composition containing 10~90% of the extracts of the present invention, when considering that the contents of powder and functional ingredient may be 10~60% in preparing the table and soft capsule, and the contents of powders and functional ingredients may be 10~90% in preparing the hard capsule.

In one embodiment of the present invention, the composition as defined above may be taken one time before, during and/or after motor. The expression 'before break' refers to evening before bedtime, 'motor' refers to a behavior exerting a muscular strength (developing activity) in common sense method, regardless of gymnastics, walking, running, cycle, golf, tennis, swimming, marathon or triathlon. The expression 'after motor' refers to 1 hour later immediately after one motor (training session), and preferably means after finishing the entire motor (training session), if there is a time interval during the motor (training). Furthermore, if the motor (exercise) lasts for a long time, for example, in the case such as marathon or triathlon, the composition of the present invention can be preferably taken during the motor (training interval).

Advantageous Effects

Accordingly, the present invention provides a composition for promoting exercise ability or muscle development, containing extracts of *Phlomis umbrosa Turcz* and *Cynanchum wilfordii* as active ingredients. The present invention is effective for the manufacture of food which promotes muscle development to enhance exercise ability, and has functionality for the promotion of muscle development or enhancement of exercise ability.

DESCRIPTION OF DRAWINGS

FIG. 1 is a result graph determining the maximum exercise ability by practicing the forced swimming movement after taking the composition of the present invention or the control composition.

FIG. 2 is a result graph determining the maximum exercise ability by practicing treadmill motor after taking the composition of the present invention or the control composition.

FIG. 3 is a result graph determining the muscle mass of gastrocnemius after taking the composition of the present invention or the control composition.

MODE FOR INVENTION

Hereinafter, the present invention will be described in detail with reference to Examples. However, the following examples are for illustrative purposes only and are not intended to limit the scope of the present invention.

Example 1

Preparation of Extracts of *Cynanchum wilfordii* and *Phlomis umbrosa Turcz* 100 g of each dried *Cynanchum wilfordii* and *Phlomis umbrosa Turcz* were crushed in the size of 2-5 mm length and then mixed with 2 L water and heated to extract while stirring them for 10 hours. The extracted solution was cooled to 70° C., and 3% of α-amylase in relation to the weight of *Cynanchum wilfordii* and *Phlomis umbrosa Turcz* was added to the extract and reacted at the temperature of 70° C. for 6 hours. The extract was heated to 95° C. for 15 minutes and then immediately quickly freeze to stop the activity of α-amylase. It was centrifugated at 15,000 rpm for 20 minutes to separate the supernatant, and then stirred at room temperature for 30 minutes after adding 20 g of activated carbon. It was filtrated at room temperature and the filtrate was concentrated and used.

Example 2

<2-1> Experimental Animal

After receiving 4-weeks-old ICR-based male mice and adopting them for one week, the experimental animals were classified into each of 5 experimental groups as follows. Three groups of a control group, an exercise group, and experimental group were set, and the experimental group and the exercise group performed the exercises described in Examples 2-2 and 2-3 everyday. In the experimental group, 3 mg/kg of the mixed extracts of *Phlomis umbrosa Turcz* and *Cynanchum wilfordii* was orally administered once a day for a total of 2 weeks, and in the control and motor groups, distilled water was administered as the control material.

<2-2> Forced Swimming Experiment

Water at 25° C. was filled in a plastic water bath (diameter 15 cm×height 22 cm) and mice were allowed to swim in the bath. On the tail of each mouse, a weight corresponding to 5% of the body weight was hanged, and then allowed to swim for 20 minutes every day for 2 weeks.

After 2 weeks, the exercise ability was determined by practicing the forced swimming experiment, together with the termination of administration of the experimental materials, and then was compared between the groups. The swimming time until the mice were exhausted was determined, and it was judged as the exhaustion when noses of the mice were sank under the surface of water and then did not come up to the surface of the water for 5 seconds or more.

As a result, as shown in FIG. 1, the exercise group taking the control material was identified that the swimming time was increased in comparison with the control group which did not exercise, but were not statistically significant. On the contrary, it was identified that the exercise time of the experimental group was significantly increased statistically compared with the control group. In the case of the mixed extracts of *Phlomis umbrosa Turcz* and *Cynanchum wilfordii* (experimental group), the swimming time was significantly enhanced statistically than the exercise group practicing the exercise.

Therefore, it was identified that the composition of the present invention has the excellent efficacy in promoting the exercise ability.

<2-3> Treadmill Test

The experimental and exercise groups performed treadmill motor (training) at a speed of 15 m/min for 20 minutes every day during the first 1 week, and performed treadmill motor at a speed of 20 m/min for 30 minutes every day during the second week. 1 A of weak electric current was flowed at the rear of the treadmill so that the mice motor exercised continuously.

After 2 weeks, the maximum exercise ability was measured together with the end of the administration of the experimental materials. The exercising time until the mice were exhausted at the speed of 20 m/min was measured, and it was judged as the exhaustion when the mice could not run on the treadmill and were pushed to the electrode to stay 10 seconds or more and did not enter the treadmill.

As a result, as shown in FIG. 2, it was identified that the running time was increased in the exercise group taking the control materials compared with the control group, but it was not statistically significant. On the contrary, it was identified that the motor time was significantly increased statistically in the experimental groups compared to the control group. It was identified that the mixed extracts of *Phlomis umbrosa Turcz* and *Cynanchum wilfordii* statistically increased the running time statistically than the exercise group practicing the same motor exercise.

Therefore, it was identified that the composition of the present invention has an excellent efficacy promoting the exercise ability.

<2-4> Determination of the Muscle Mass of Gastrocnemius

At the end of two week-period for taking the experimental materials, the mice were sacrificed and gastrocnemius was separated and weighed.

As a result, as shown in FIG. 3, it was identified that the muscle mass of gastrocnemius was increased in the exercise group taking the control materials compared to the control group not performed exercise, but it was not statistically significant. On the contrary, it was identified that the muscle mass of gastrocnemius in the experimental group was significantly increased statistically compared to the control group. It was identified that the mixed extracts of *Phlomis umbrosa Turcz* and *Cynanchum wilfordii* significantly increased the muscle mass of gastrocnemius statistically compared to the exercise group performing the exercise.

Therefore, it was identified that the composition of the present invention has the excellent efficacy promoting muscle development.

The invention claimed is:

1. A food composition for promoting exercise ability, comprising an active ingredient consisting of a mixture of *Phlomis umbrosa Turcz* extract and *Cynanchum wilfordii* extract, wherein the *Phlomis umbrosa Turcz* extract and the *Cynanchum wilfordii* extract is contained in a 1:1 weight ratio.

2. The food composition according to claim 1, wherein the extracts of the *Phlomis umbrosa Turcz* and *Cynanchum wilfordii* are extracted with any one of solvents selected from the group consisting of water, alcohol having 1 to 6 carbon atoms and the mixed solvents thereof.

3. A food composition for promoting muscle development, comprising an active ingredient consisting of a mixture of *Phlomis umbrosa Turcz* extract and *Cynanchum wilfordii* extract, wherein the *Phlomis umbrosa Turcz* extract and the *Cynanchum wilfordii* extract is contained in a 1:1 weight ratio.

4. The food composition according to claim 3, wherein the extracts of the *Phlomis umbrosa Turcz* and *Cynanchum wilfordii* are extracted with any one of solvents selected from the group consisting of water, alcohol having 1 to 6 carbon atoms and the mixed solvents thereof.

5. A pharmaceutical composition for promoting exercise ability and promoting muscle development, comprising an active ingredient consisting of a mixture of *Phlomis umbrosa Turcz* extract and *Cynanchum wilfordii* extract, wherein the *Phlomis umbrosa Turcz* extract and the *Cynanchum wilfordii* extract is contained in a 1:1 weight ratio.

6. The pharmaceutical composition according to claim 5, wherein the extracts of the *Phlomis umbrosa Turcz* and *Cynanchum wilfordii* are extracted with any one of solvents selected from the group consisting of water, alcohol having 1 to 6 carbon atoms and the mixed solvents thereof.

* * * * *